United States Patent
Buddery et al.

(10) Patent No.: US 10,751,062 B2
(45) Date of Patent: Aug. 25, 2020

(54) MEDICAL DEVICE FOR TEMPORARY DEPLOYMENT INTO A BODILY LUMEN

(71) Applicant: Cook Medical Technologies LLC, Bloomington, IN (US)

(72) Inventors: Alexander Buddery, Chelmer (AU); Joshua Griffin, Greenslopes (AU); Roger Wilkinson, Everton Park (AU)

(73) Assignee: Cook Medical Technologies LLC, Bloomington, IN (US)

( * ) Notice: Subject to any disclaimer, the term of this patent is extended or adjusted under 35 U.S.C. 154(b) by 200 days.

(21) Appl. No.: 15/901,015

(22) Filed: Feb. 21, 2018

(65) Prior Publication Data
US 2018/0235638 A1 Aug. 23, 2018

Related U.S. Application Data

(60) Provisional application No. 62/461,478, filed on Feb. 21, 2017.

(30) Foreign Application Priority Data

Feb. 21, 2017 (AU) .................................. 2017201160

(51) Int. Cl.
*A61F 2/06* (2013.01)
*A61B 17/12* (2006.01)
(Continued)

(52) U.S. Cl.
CPC ........ *A61B 17/12109* (2013.01); *A61B 17/11* (2013.01); *A61B 17/1204* (2013.01);
(Continued)

(58) Field of Classification Search
CPC .............. A61B 17/12; A61B 17/12109; A61B 17/1204; A61F 2/95; A61F 2/958;
(Continued)

(56) References Cited

U.S. PATENT DOCUMENTS

| 5,730,698 A | 3/1998 | Fischell et al. |
| 6,143,015 A | 11/2000 | Nobles |

(Continued)

FOREIGN PATENT DOCUMENTS

| AU | 2010254599 B1 | 2/2011 |
| AU | 2017201160 | 4/2017 |

(Continued)

*Primary Examiner* — Vi X Nguyen
(74) *Attorney, Agent, or Firm* — Kevin L. Leffel

(57) ABSTRACT

A medical device for temporary deployment into a bodily lumen is provided. The medical device comprises: a guide wire cannula having a proximal end and a distal end; a tip attached to the proximal end of the guide wire cannula; a pusher having a proximal and a distal end, the pusher having a through-bore disposed around the guide wire cannula; and a temporary stent assembly having a proximal end attached to the tip and a distal end adjacent to the proximal end of the pusher. The temporary stent assembly comprises a covered portion. The covered portion has a proximal sealing zone, a distal sealing zone and a recess between the proximal and distal sealing zones.

15 Claims, 14 Drawing Sheets

(51) Int. Cl.
*A61F 2/90* (2013.01)
*A61F 2/856* (2013.01)
*A61F 2/962* (2013.01)
*A61B 17/11* (2006.01)
*A61B 17/34* (2006.01)
*A61B 17/00* (2006.01)
*A61F 2/95* (2013.01)
*A61F 2/82* (2013.01)

(52) U.S. Cl.
CPC .... *A61B 17/1215* (2013.01); *A61B 17/12045* (2013.01); *A61B 17/12145* (2013.01); *A61F 2/06* (2013.01); *A61F 2/856* (2013.01); *A61F 2/90* (2013.01); *A61F 2/962* (2013.01); *A61B 17/00234* (2013.01); *A61B 17/3421* (2013.01); *A61B 2017/1107* (2013.01); *A61B 2017/1139* (2013.01); *A61B 2017/1205* (2013.01); *A61F 2/95* (2013.01); *A61F 2002/823* (2013.01); *A61F 2002/826* (2013.01)

(58) Field of Classification Search
CPC .. A61F 2/966; A61F 2/954; A61F 2/06; A61F 2/07
See application file for complete search history.

(56) References Cited

U.S. PATENT DOCUMENTS

| | | | |
|---|---|---|---|
| 8,052,639 | B2 | 11/2011 | Wilson |
| 2005/0021123 | A1* | 1/2005 | Dorn .................. A61F 2/95 623/1.11 |
| 2008/0195125 | A1 | 8/2008 | Hoffman |
| 2011/0106234 | A1* | 5/2011 | Grandt .................. A61F 2/86 623/1.11 |
| 2014/0277565 | A1 | 9/2014 | Clere |
| 2015/0081005 | A1 | 3/2015 | Headley, Jr. et al. |

FOREIGN PATENT DOCUMENTS

| | | |
|---|---|---|
| CN | 102973303 | 3/2013 |
| CN | 102973303 A | 3/2013 |
| EP | 2322118 B1 | 5/2011 |
| WO | 0067673 A1 | 11/2000 |
| WO | WO 0067673 A1 | 11/2000 |
| WO | 2003068306 A1 | 8/2003 |
| WO | WO 2003-068306 A1 | 8/2003 |
| WO | 2006023331 A1 | 3/2006 |
| WO | WO 2006-023331 A1 | 3/2006 |

* cited by examiner

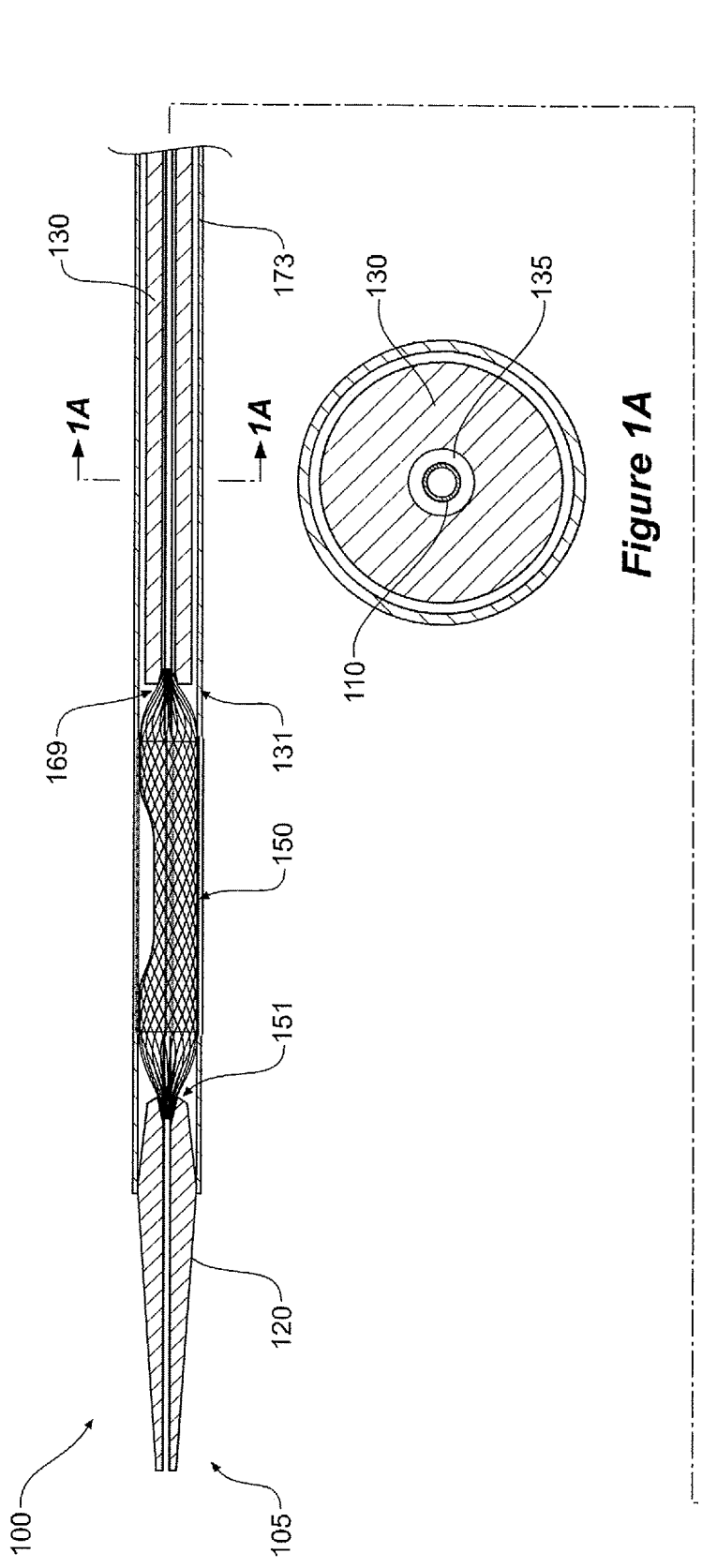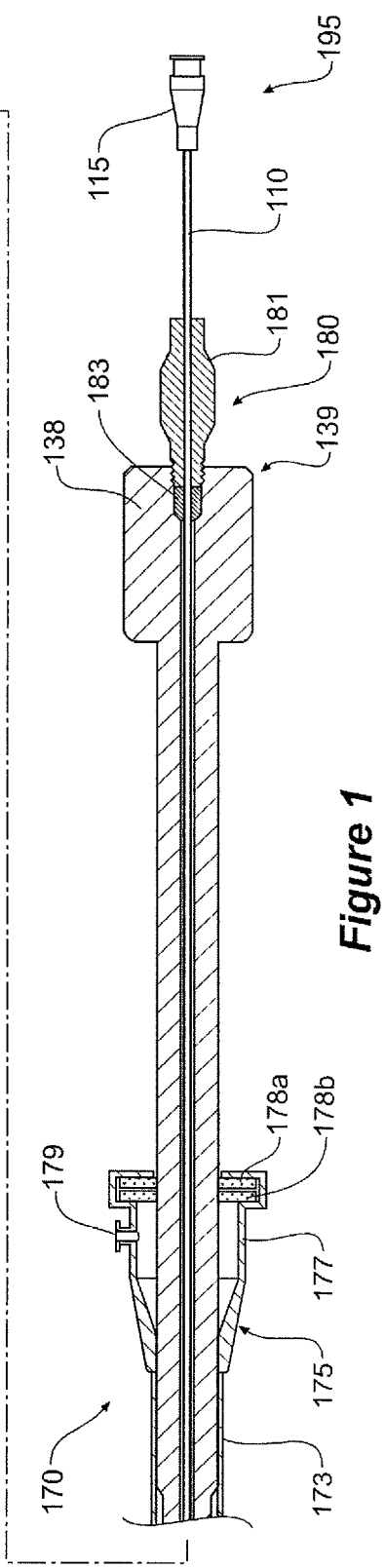
*Figure 1A*
*Figure 1*

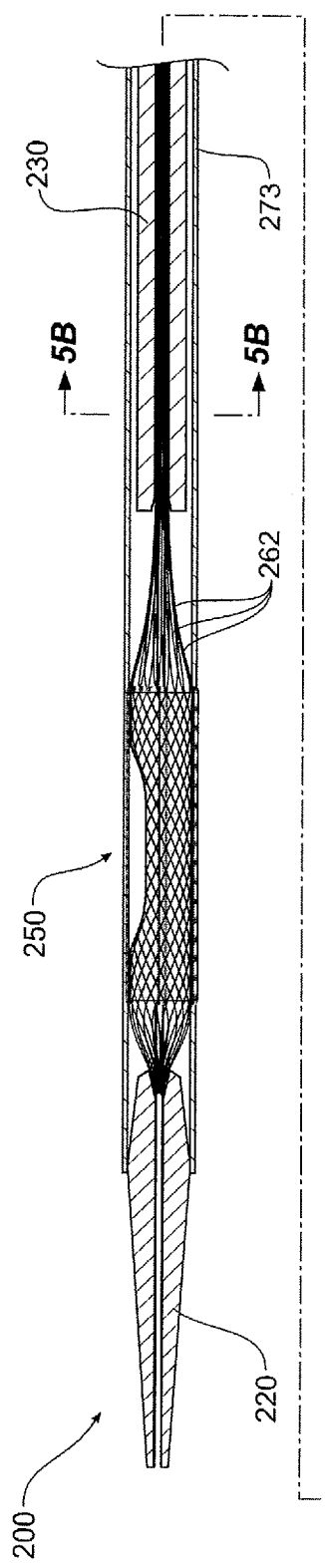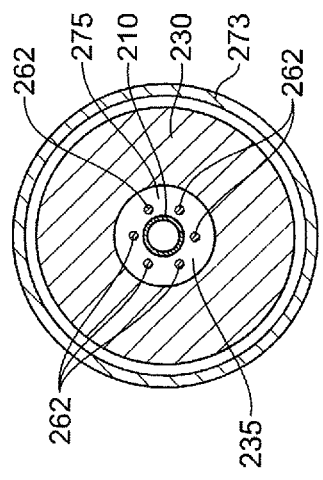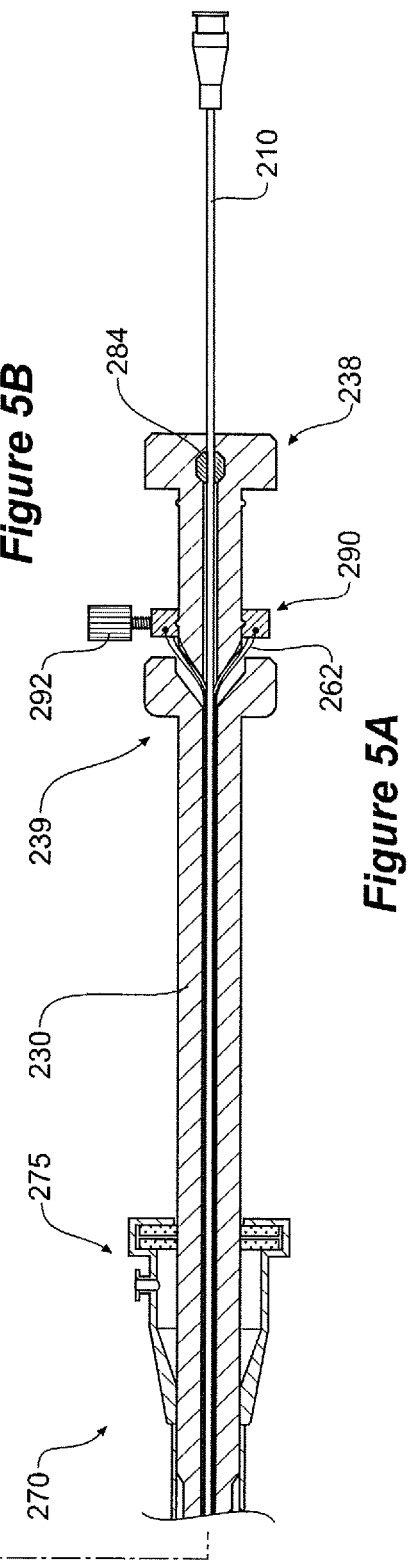

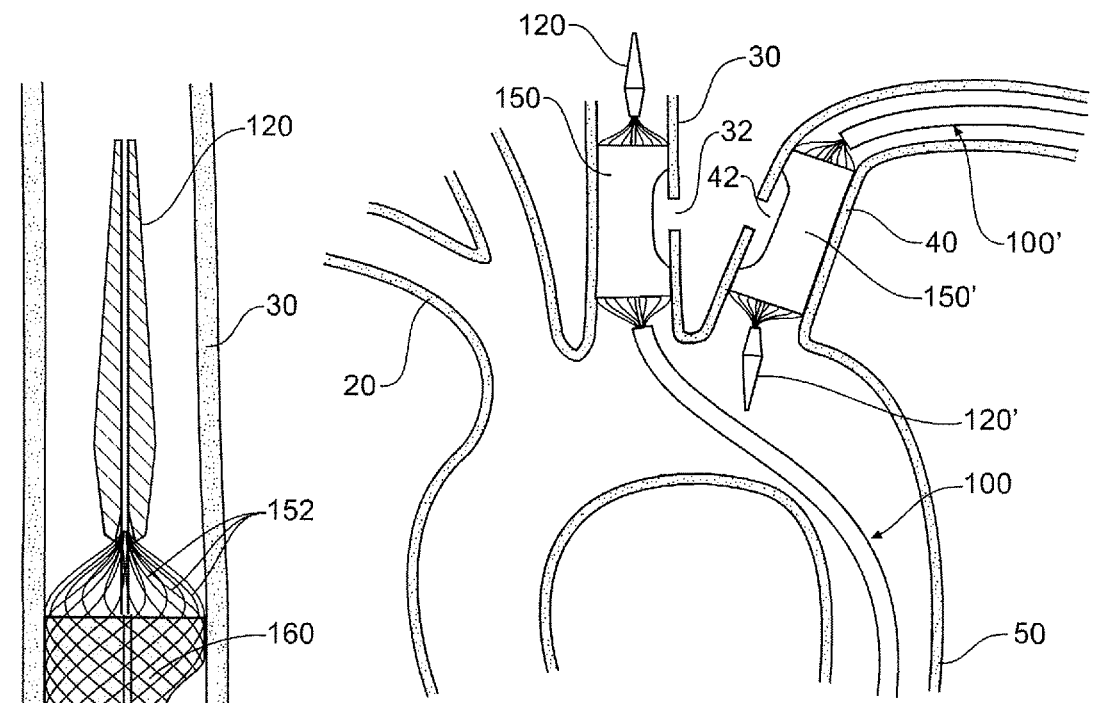
Figure 10A
Figure 11
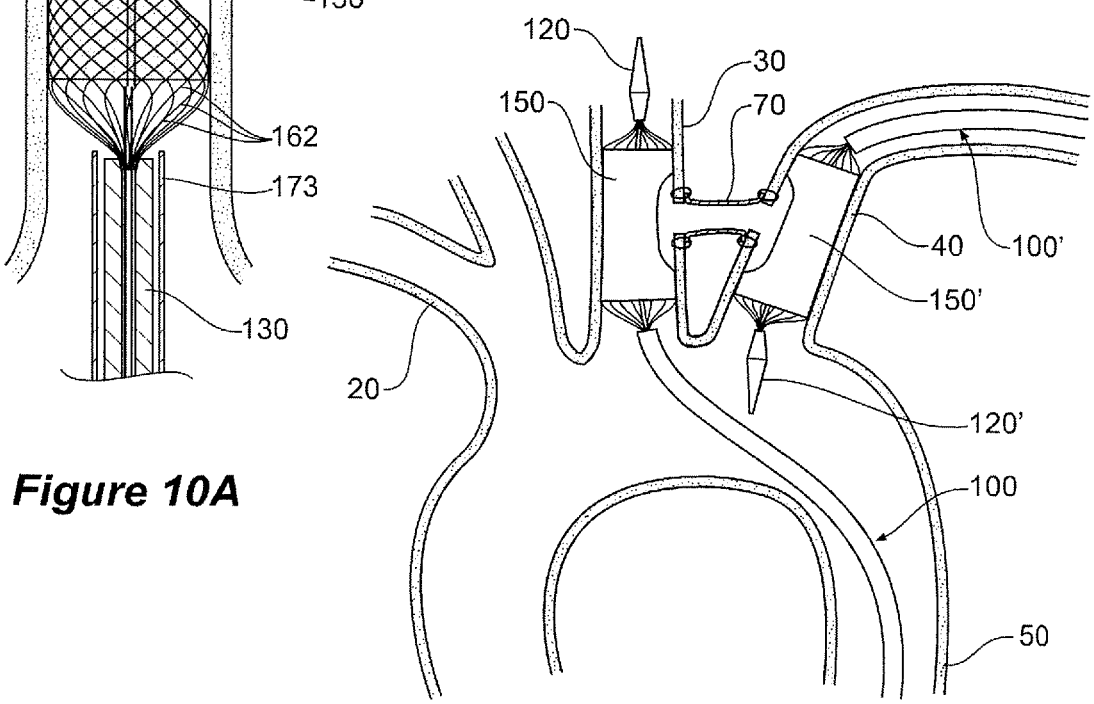
Figure 12

MEDICAL DEVICE FOR TEMPORARY DEPLOYMENT INTO A BODILY LUMEN

TECHNICAL FIELD

The present disclosure relates generally to the field of medical devices. Particular embodiments are related to medical devices that are deployable into bodily lumens including vascular systems.

BACKGROUND OF THE INVENTION

A variety of medical devices have been developed for endovascular repair. For instance various methods and devices have been developed to repair aneurysmal or occluded branches of the aorta. Devices and techniques have also been developed to bypass or cross-connect between adjacent arteries or other channels of the body. For instance, anastomosis procedures to join two or more arteries to that branch from the aortic arch are known. Commonly such techniques involve clamping and partial or total occlusion of aortic blood vessels. The resultant interruption of blood flow increases stress on the heart, potentially causing cardiac morbidity. Occlusion of blood flow also can lead to ischemia for downstream organs and extremities potentially leading to other complications. Furthermore, the act of placing occlusive clamps across diseased blood vessels risks injury because the aorta itself is often diseased. In addition, plaque along the arterial wall is potentially disturbed to embolise, which is highly undesirable.

There is a need to provide improved medical devices that facilitate the continuation of blood flow during bypass or anastomosis procedures. There is also a need for medical devices that ameliorate at least some of the disadvantages associated with existing procedures, including those mentioned above.

Throughout this specification, the term "distal" with respect to a portion of the aorta, a deployment device or an endograft means the end of the aorta, deployment device or endograft further away in the direction of blood flow from the heart and the term "proximal" means the portion of the aorta deployment device or end of the endograft nearer to the heart in the direction of blood flow. When applied to other vessels, similar terms such as caudal and cranial should be understood.

SUMMARY OF THE INVENTION

According to a first aspect of the invention, there is provided a medical device for temporary deployment into a bodily lumen, the medical device comprising:
 a guide wire cannula having a proximal end and a distal end;
 a tip attached to the proximal end of the guide wire cannula;
 a pusher having a proximal and a distal end, the pusher having a through-bore disposed around the guide wire cannula; and
 a temporary stent assembly having a proximal end attached to the tip and a distal end adjacent to the proximal end of the pusher, the temporary stent assembly comprising a covered portion, the covered portion having a proximal sealing zone, a distal sealing zone and a recess between the proximal and distal sealing zones.

In one form, the temporary stent assembly comprises a plurality of proximal connecting lines extending from the tip to the covered portion and a plurality of distal connecting lines extending from the covered portion to the pusher.

In one form, the temporary stent assembly is self-expanding.

In one form, the covered portion comprises a blood impermeable material supported by woven metal, the woven metal operable to self-expand the blood impermeable material.

In one form, the recess is shaped such that, in use within an artery, a pocket is formed between the proximal and distal sealing zones of the covered portion.

In one form, the proximal sealing zone has a first minimum perimeter and the recess has a second minimum perimeter, the second minimum perimeter shorter than the first minimum perimeter.

In one form, the temporary stent assembly is longitudinally stretchable from a deployable position to a re-sheathable position.

In one form, the medical device further comprises a sheath assembly disposed over the pusher, the sheath assembly comprising:
 a sheath manipulator at a distal end thereof; and
 a sheath extending proximally from the sheath manipulator,
 whereby the sheath assembly is slidably movable with respect to the pusher from a first position in which the sheath covers the temporary stent assembly to a second position in which at least the covered portion of the temporary stent assembly is uncovered by the sheath.

In one form, the sheath assembly comprises a seal assembly at distal end thereof, the seal assembly operable to minimize the egress of blood from the sheath assembly.

In one form, the tip is extendible from the pusher so as to stretch the temporary stent assembly.

In one form, the pusher comprises a grippable handle at its distal end.

In one form, the pusher includes a mechanism for selectively holding the guide wire cannula to the handle and releasing the guide wire cannula from the handle.

In one form, the medical device further comprises a line manipulator located at the distal end of the pusher, the line manipulator manipulable to pull the distal lines of the temporary stent assembly in a direction away from the tip as to stretch the temporary stent assembly.

In one form, the distal lines of the temporary stent assembly pass through the through-bore.

In one form, the line manipulator is lockable in a deploying position in which the temporary stent assembly is not stretched.

In one form, the line manipulator is lockable in a re-sheathable position in which the temporary stent assembly is stretched.

In one form, the proximal connecting lines and the distal connecting lines comprise wire lines.

In one form, the wire lines comprise nitinol wire.

According to a second aspect of the invention, there is provided a medical device for temporary deployment into a bodily lumen, the assembly comprising:
 a guide wire cannula having a proximal end and a distal end;
 a tip attached to the proximal end of the guide wire cannula;
 a pusher having a proximal and a distal end, the pusher having a through-bore disposed around the guide wire cannula;
 a sheath assembly disposed over the pusher, the sheath assembly comprising: a sheath manipulator at a distal end thereof; and a sheath extending proximally from the sheath manipulator; and a temporary stent assembly having a proximal end attached to the tip and a distal end adjacent to the proximal end of the pusher, the temporary stent assembly comprising a covered portion, the covered portion comprising impermeable material supported by woven metal and having a proximal sealing zone, a distal sealing zone and a recess between the proximal and distal sealing zones, wherein the temporary stent assembly comprises a plurality of proximal connecting lines extending from the tip to the covered portion and a plurality of distal connecting lines extending from the covered portion to the pusher; and wherein the stent is longitudinally stretchable from a deployable position to a re-sheathable position, whereby the sheath assembly is slidably movable with respect to the pusher from a first position in which the sheath covers the temporary stent assembly to a second position in which at least the covered portion of the temporary stent assembly is uncovered by the sheath.

According to a third aspect of the invention, there is provided a method of establishing a bypass graft between two arteries, the method comprising the steps of:

deploying a first temporary stent assembly into a first target artery, the first temporary stent assembly having a first covered portion having a first proximal sealing zone, a first distal sealing zone and a first recess between the first proximal and distal sealing zones;

deploying a second temporary stent assembly into a second target artery adjacent to the first target artery, the second temporary stent assembly having a second covered portion having a second proximal sealing zone, a second distal sealing zone and a second recess 265 between the second proximal and distal sealing zones;

installing an anastomosis stent between the first and second target arteries, the anastomosis stent bridging between the first recess and the second recess of the first and second temporary stent assemblies; and retrieving the first and second temporary stent assemblies, thereby establishing an anastomosis between the first and second target arteries.

BRIEF DESCRIPTION OF THE DRAWINGS

FIG. 1 is a diagrammatic cross-sectional view of a first embodiment of the invention.

FIG. 1A is a diagrammatic cross-sectional view taken through section lines 1A-1A shown on FIG. 1.

FIGS. 2A and 2B are cross-sectional views taken through section lines to 2A-2A and 2B-2B shown on FIG. 2 respectively.

FIG. 5A is a diagrammatic cross-sectional of a variant of the embodiment shown in FIG. 5.

FIG. 5B is a diagrammatic cross-sectional view taken through section lines 5B-5B shown on FIG. 5A.

FIG. 10A is a magnified and more detailed view of a portion of the left common carotid artery and a portion of one of the medical devices shown in FIG. 10.

FIG. 11 is a similar view to that of FIG. 10, but shows the anatomy after incisions have been made in the left common carotid artery and the left subclavian artery.

FIG. 12 is a similar view to that of FIG. 11, but shows the anatomy after installation of a anastomosis graft between the less common carotid artery and the left subclavian artery.

DETAILED DESCRIPTION

Referring to FIGS. 1 to 4, a medical device 100 according to an embodiment of the invention is shown. The medical device 100 is temporarily deployable into a bodily lumen such as an artery.

Figure 1B:
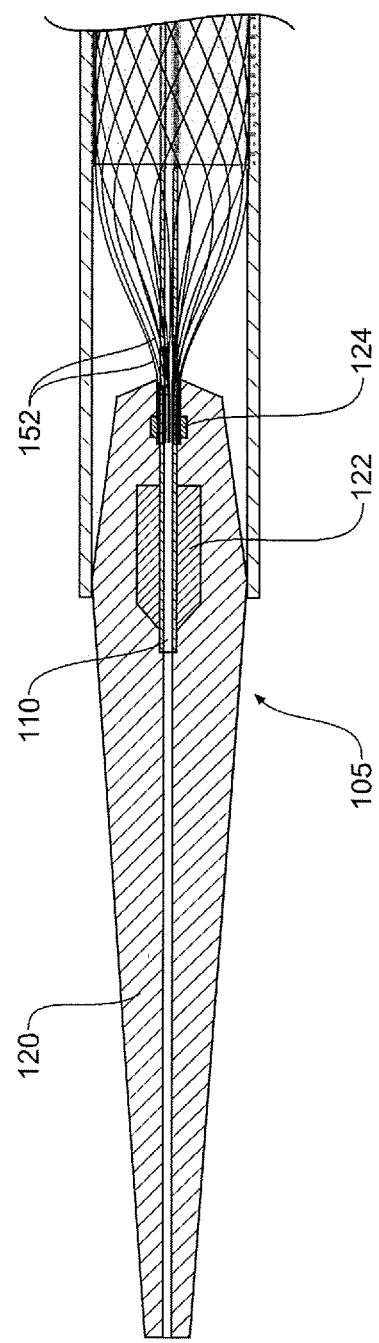
FIG. 1B is a detailed view of a dilator tip that may form part of the embodiment of the invention shown in FIG. 1.

The medical device 100 comprises a guide wire cannula 110 having a proximal end 105 and a distal end 195. The guide wire cannula 110 may be made from a flexible thin-walled metal tube. Biocompatible metals such as stainless steel or nitinol may be used. A tip 120 is attached to the proximal end 105 of the guide wire cannula 110. The tip 120 is atraumatic and may be formed from soft nylon or radiopaque urethane material. The tip 120 can be described as a dilator tip as its shape allows it to dilate a vessel as it is advanced through the vessel along a guide wire. The shape also facilitates entry (for instance though the femoral artery). As can be seen in FIGS. 1 and 1B, for instance, the tip 120 is conical and tapers inwards towards the guide wire in a proximal direction.

FIG. 1B is a detailed view of an example of the tip 120 and the proximal end 105 of the guide wire cannula. The conical tip 120 is secured to the guide wire cannula 110 using an attacher 122. Gluing or moulding methods may be employed.

A pusher 130, having a proximal and distal end 131,139 also forms part of the medical device 100. The pusher 130 has a through bore 135 disposed around the guide wire cannula 110. This is most clearly shown in the two cross-sectional views of FIG. 1 and FIG. 1A. In particular FIG. 1A, a cross-sectional view through section 1A-1A shown on FIG. 1, clearly shows the pusher 130 around the guide wire cannula 110. The through bore 135 is also clearly illustrated in FIG. 1A. The internal diameter of the through bore 135 can be varied with respect to the external diameter of the guide wire cannula 110 to provide differing levels of clearance.

The pusher 130 illustrated is "thick walled", that is the thickness of its wall is several times greater than that of the guide wire cannula 110. In some instances, the pusher 130 and the guide wire cannula 110 are the same component, having different outer diameters at the location at which a temporary stent assembly is to be carried.

The medical device 100 also includes a temporary stent assembly 150, which is also shown in FIGS. 1 to 4. The temporary stent assembly 150 is perhaps most clearly shown in FIGS. 2, 2A and 2B. As can be seen in these figures, the temporary stent assembly 150 has a proximal end 151 attached to the tip 120 and a distal end 169 attached to the proximal end 131 of the pusher 130.

The temporary stent assembly 150 has a covered portion 160. The covered portion 160, most clearly shown in FIG. 2, has a proximal sealing zone 153, a distal sealing zone 163 and a recess 165 between the proximal and distal sealing zones 153,163.

The temporary stent assembly 150 includes the plurality of proximal connecting lines 152 extending from the tip 120 to the covered portion 160 and a plurality of distal connecting lines 162 extending from the cupboard portion 160 to the pusher 130. The connecting lines 152,162 are made from nitinol in the embodiment illustrated. In other embodiments, the lines may be made from any suitable biocompatible material. These materials could include stainless steel, cobalt-chromium or tungsten.

The proximal connecting lines 152 maybe connected to the tip 120 in any suitable way. For instance, they may be crimped into a metal ring 124 (swaged) onto the guide wire cannula 110 as is shown in FIG. 1B. The tip may be moulded over the guide wire cannula 110, the connector 122 and the metal ring 124.

Figure 2:
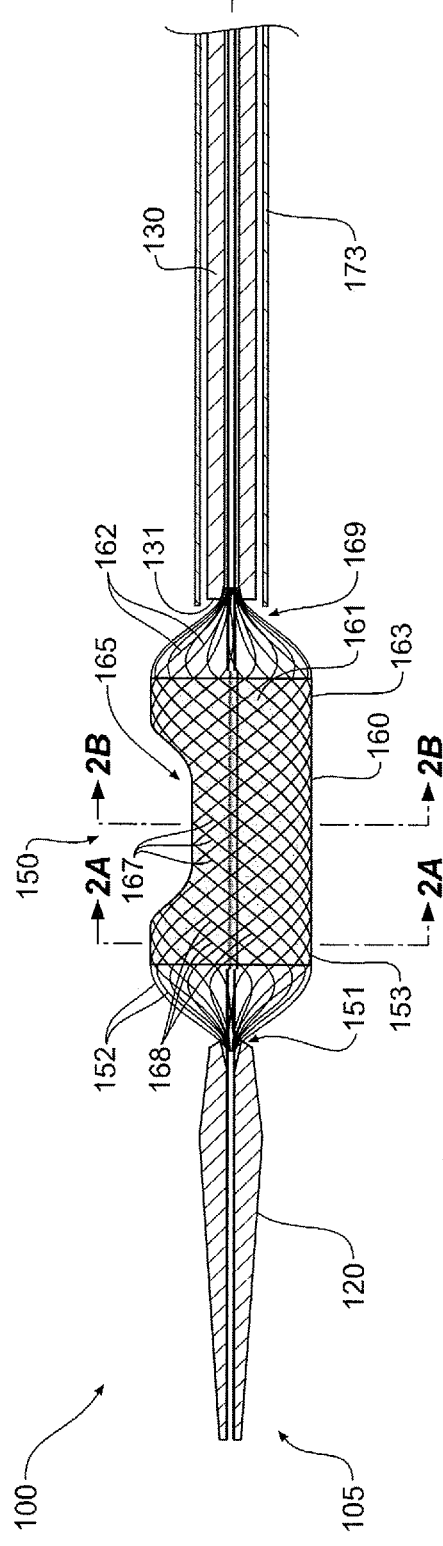
FIG. 2 is a similar view to that of FIG. 1 but shows the medical device in a deployed condition.
Figure 2:
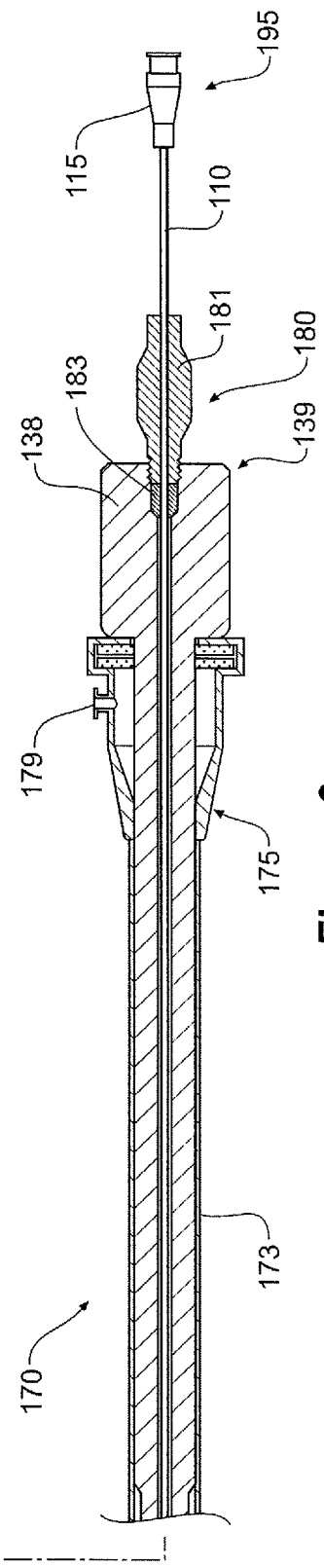

Referring to FIG. 2, together with FIGS. 2A and 2B, it can be seen that the covered portion 160 includes a woven metal section comprising self-expanding supports 167 and 168. These self expanding supports are nitinol wires in the embodiment illustrated. In other embodiments other materials can be used. The self-expanding supports are adjacent to or integrated with the blood impermeable material 161. The blood impermeable material can include polytetrafluoroethylene, Dacron, polyamide Thoralon™, silicone or any other suitable biocompatible graft material. The blood impermeable material need only be partially impermeable to blood given that the device is designed for temporary deployments. That is, the material need only be blood impermeable from a practical perspective. Small amounts of blood leakage may be permissible for many uses. The blood impermeability is important however to ensure that there is not massive blood flow through the cupboard portion between the proximal sealing zone 153 and the distal sealing zone 163.

The wires may be embedded in the material of the covered portion 160 by casting over the wires. Alternatively, the material of the covered portion 160 may be woven through the wires. In alternative embodiments, the material could be sutured to the wires.

The recess 165, most clearly shown in FIGS. 2 and 9B, is shaped such that, in use, within an artery, such as the common carotid artery 30 illustrated in FIG. 9B, a pocket 35 is formed between the proximal and distal sealing zones 153 and 163 of the covered portion 160.

The recess 165 allows the temporary stent assembly 150 to be spaced away from a target anastomosis location, thereby allowing a incision to be made and an anastomosis stent to be sutured in place without undue interference from the temporary stent assembly 150. As described above, the covered portion 160 includes a woven metal section. This woven metal section protects the covered portion from excessive damage that may arise from accidental scalpel contact.

Referring to FIGS. 2A and 2B, taken through section lines to 2A-2A and 2B-2B respectively shown on FIG. 2, it can be seen that the proximal sealing zone has a first minimum perimeter 153p and the recess 165 has a second minimum perimeter 165p shorter than the first minimum perimeter 153p. This facilitates the creation of the recess 165.

The temporary stent assembly 150 may include markers such as gold to aid visibility of key features under x-ray fluoroscopy. The temporary stent assembly 150 may also include tactile markers such as raised sections at the bounds of the recess 165 to allow the physician to see the placement of the device from the outer surface of the target vessel.

Figure 3:
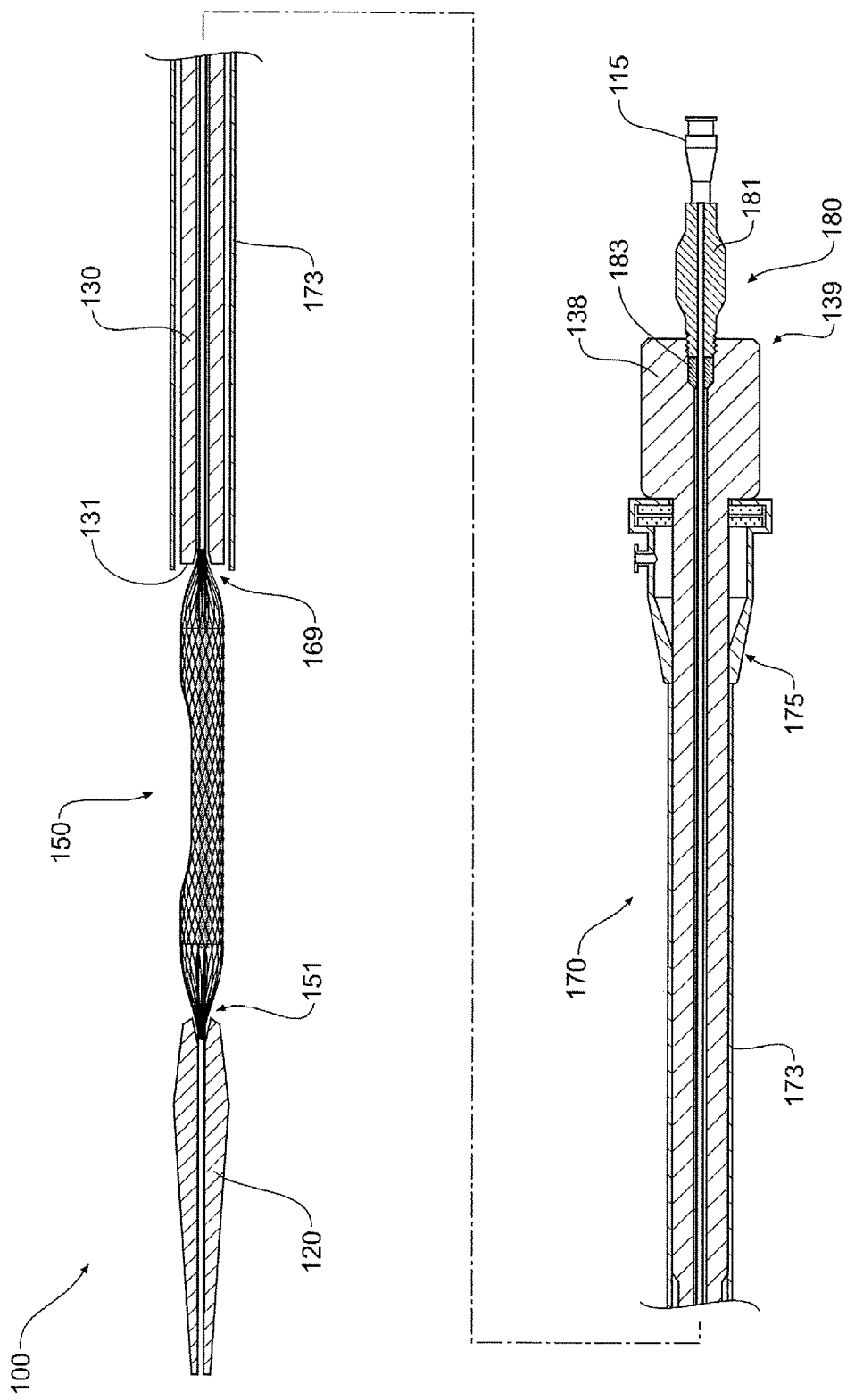
FIG. 3 is a similar view to that of FIGS. 1 and 2 but shows the medical device in a condition ready for re-sheathing of the temporary stent assembly.
Figure 4:
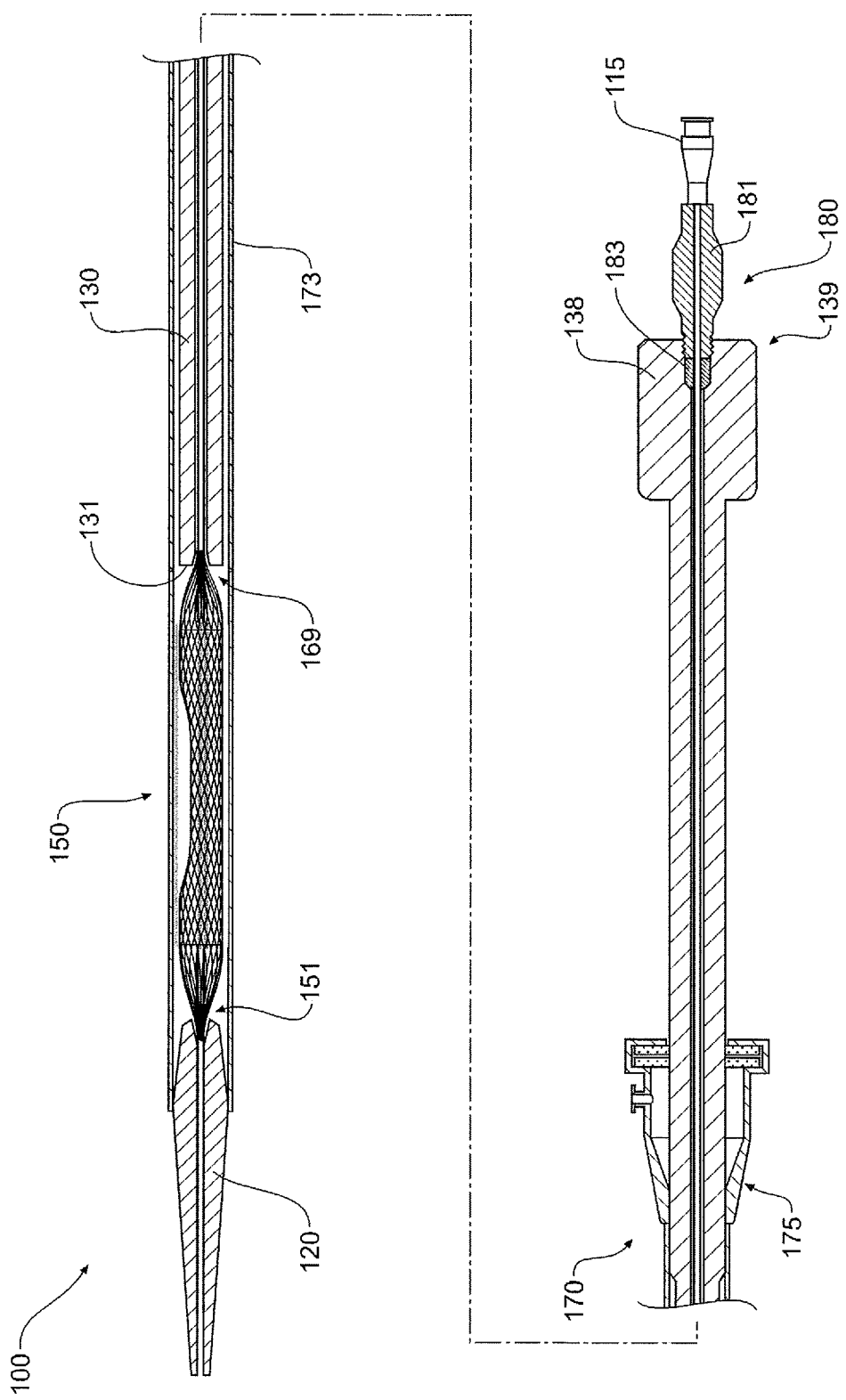
FIG. 4 is a similar view to that of FIGS. 1, 2 and 3 but shows the medical device in a re-sheathed condition.

The temporary stent assembly 150 is longitudinally stretchable from a deployable position, such as the position shown in FIG. 2, to a re-sheathable position, such as the position shown in FIGS. 3 and 4. Referring to FIG. 3, it can be seen that the distance between the tip 120 and the proximal end 131 has been increased. This increase in length stretches the temporary stent assembly 150 making it easier to re-sheath. FIG. 4 shows the temporary stent assembly 150 re-sheathed.

Returning to FIG. 1, it can be seen that the medical device 100 further comprises a sheath assembly 170 disposed over the pusher 130. The sheath assembly 170 includes a sheath manipulator 175 of the distal end thereof and a sheath 173 extending proximally from the sheath manipulator 175. The sheath assembly 170 is slidably movable with respect to the pusher 130 from a first position, shown in FIG. 1, in which the sheath 173 covers the temporary stent assembly 150 to a second position in which at least the covered portion 160 of the temporary stent assembly 150 is uncovered by the sheath 173 as is shown in FIG. 2.

The sheath assembly includes a haemostatic seal assembly 177 (such as a Captor™ valve) and a flushing port 179, both at a distal end thereof. The seal assembly is operable to minimize the egress of blood from the sheath assembly, while at the same time allowing sliding movement of the pusher 130 with respect to the sheath 173. Disc seals 178a and 178b are shown in FIG. 1, however other types of seals such as wiper seals may be provided.

A flushing port 179 enables supply of flushing fluid to allow, for instance, flushing with sterile saline solution between the pusher 130 and the sheath 173 to eliminate air, while the device 100 is outside of the patient.

In different embodiments of the medical device, differing arrangements may be used so as to allow stretching of the temporary stent assembly 150. For instance, with the embodiment shown in FIGS. 1 to 4, the tip 120 is extendable from the pusher 130 so as to stretch the temporary stent assembly 150. It can be seen from FIGS. 1 to 4 that the pusher 130 includes a grippable handle 138 at its distal end 139. Within the grippable handle is a mechanism for selectively holding the guide wire cannula 110 to the handle 138 and releasing the guide wire cannula 110 from the handle 138. While various mechanisms may be used, in the embodiment illustrated a pin vice assembly is used. The pin vice assembly 180 includes a pin vice knob 181 and a pin vice clamp 183. The knob 181 has a screw thread which engages with a screw thread in the rear of the handle 138. Rotation of the knob 181 causes the knob 181 to engage against a clamp member 183 and this in turn causes the clamp member 183 to clamp against the outer rigid tube that forms the guide wire cannula 110. This prevents movement of the guide wire cannula 110 with respect to the handle 138.

A Luer lock connector 115 is also shown in FIGS. 1 to 4. The Luer lock connector 115 allows flushing with sterile saline solution to eliminate air while the device 100 is outside of the patient.

A second embodiment of the invention is shown in FIGS. 5 to 8. This second embodiment of the invention is, in many respects, similar to the first embodiment of the invention, but the arrangement for longitudinally stretching the temporary stent assembly 150, 250 from a deployable position to a receivable position is different. With the second embodiment of the invention, the medical device 200 does not rely on the tip 220 being extendable from the pusher 230 to stretch the temporary stent assembly 250. Instead, a line manipulator 290 is provided. The line manipulator 290 is located at the distal end 239 of the pusher to 230. The line manipulator 290 is manipulable to pull the distal lines 262 of the temporary stent assembly 250 in a direction away from the tip 220 so as to stretch the temporary stent assembly 250.

Figure 5:
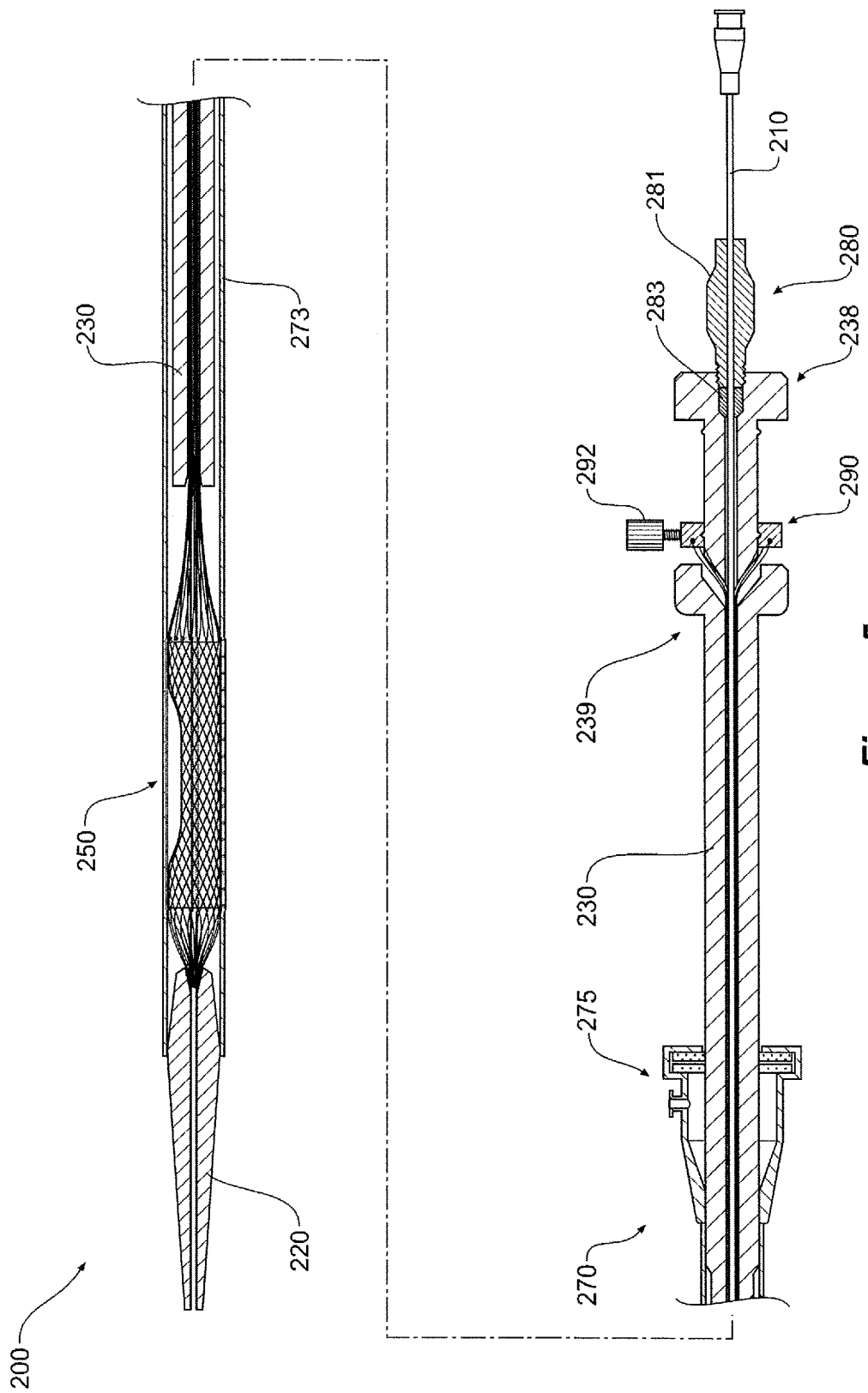
FIG. 5 is a diagrammatic cross-sectional view of a second embodiment of the invention.

Because the medical device 200, according to the second embodiment of the invention, does not rely on the tip 220 being extendable from the pusher 230 to stretch the temporary stent assembly 250, a pin vice assembly 280 (and its pin vice 283 and associated pin vice clamp) shown in FIG. 5 is not essential. FIG. 5A shows the medical device 200 without a pin vice assembly 280. Instead, a permanent retainer 284 is provided. This retainer 284 can be moulded into the handle 238 or attached in other ways.

Referring now to FIG. 5B, a diagrammatic cross-sectional view taken through section lines 5B-5B shown on FIG. 5A, it can be seen that the distal lines 262 of the temporary stent assembly 250 pass through a through bore 235 disposed around the guide wire cannula 210.

Figure 6:
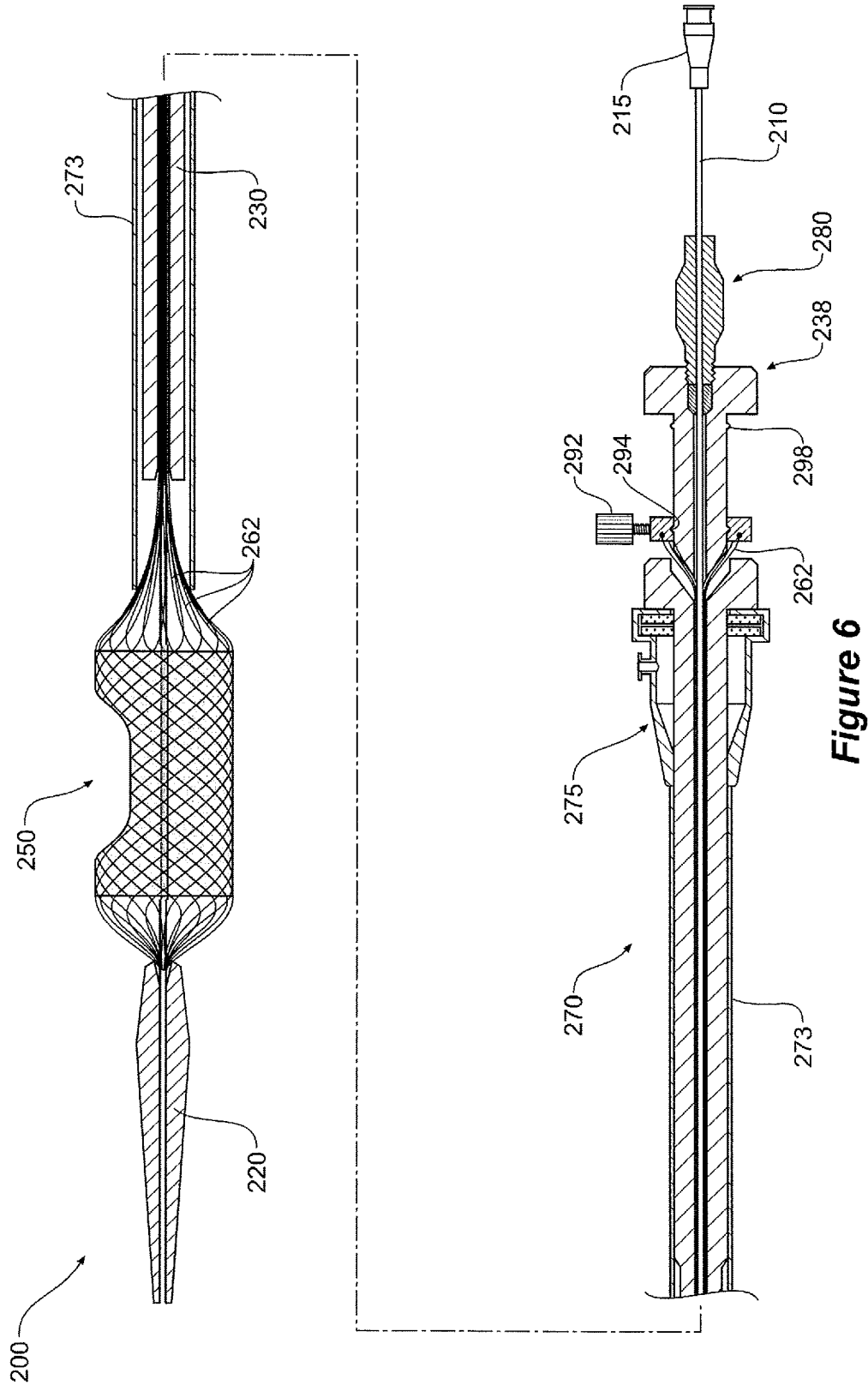
FIG. 6 is a similar view to that of FIG. 5, but shows the medical device in a deployed condition.
Figure 7:
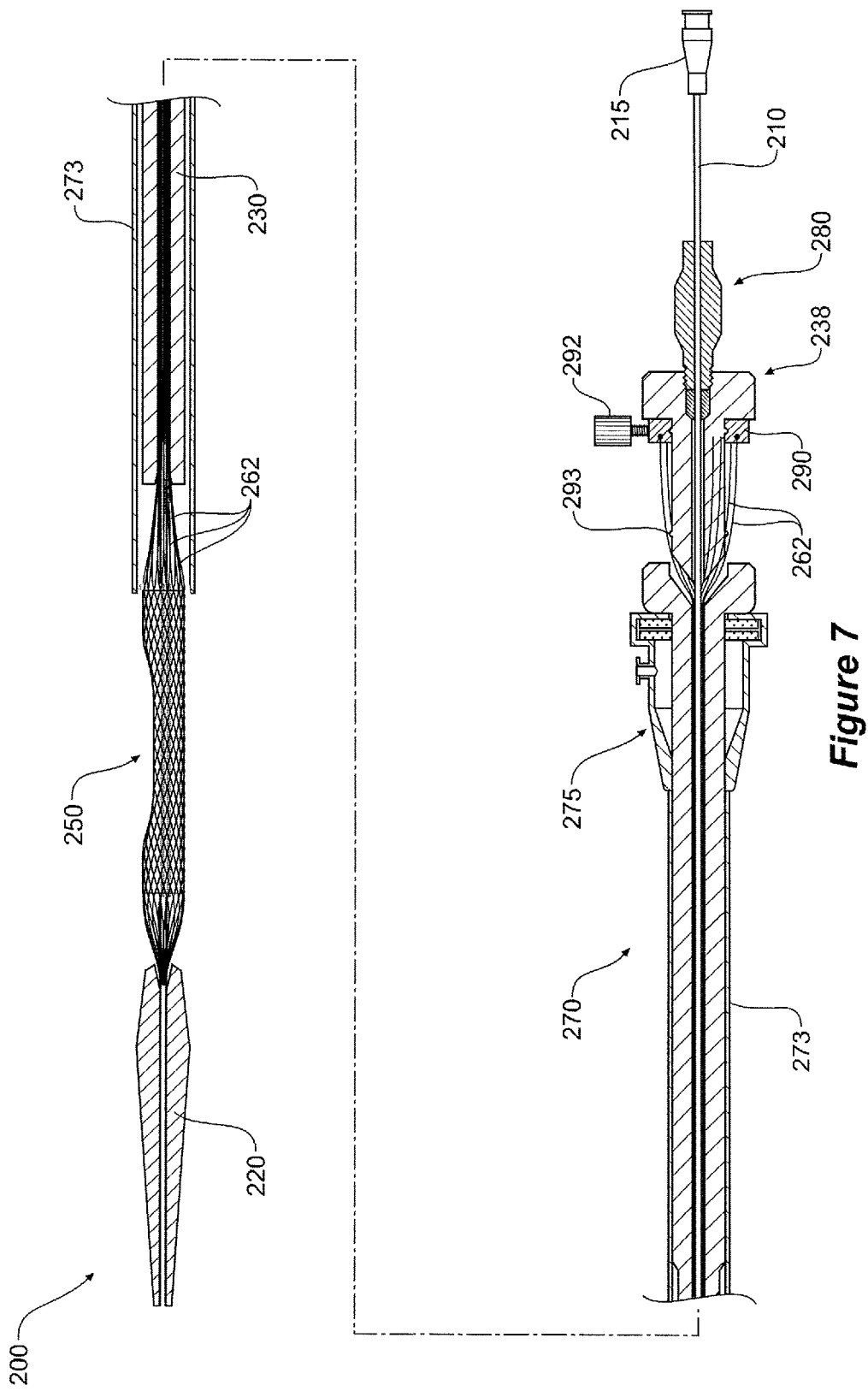
FIG. 7 is a similar view to that of FIGS. 5 and 6, but shows the medical device in a condition ready for re-sheathing of the temporary stent assembly.

The line manipulator 290 is lockable in a deploying position in which the temporary stent assembly 250 is not stretched. FIGS. 5, 5A and 6 show the line manipulator 290 in its deploying position. Detent grooves 294 interact with proximal detent protrusion 293 to hold the line manipulator 290 in this position. An optional line manipulator lock 292 is also provided to prevent inadvertent movement of the line manipulator. FIG. 7 shows the line manipulator 290 in a re-sheathable position in which the temporary stent assembly 250 is stretched. Again, in this position the detent groove 294 is engaged with the distal detent protrusion 298.

Figure 8:
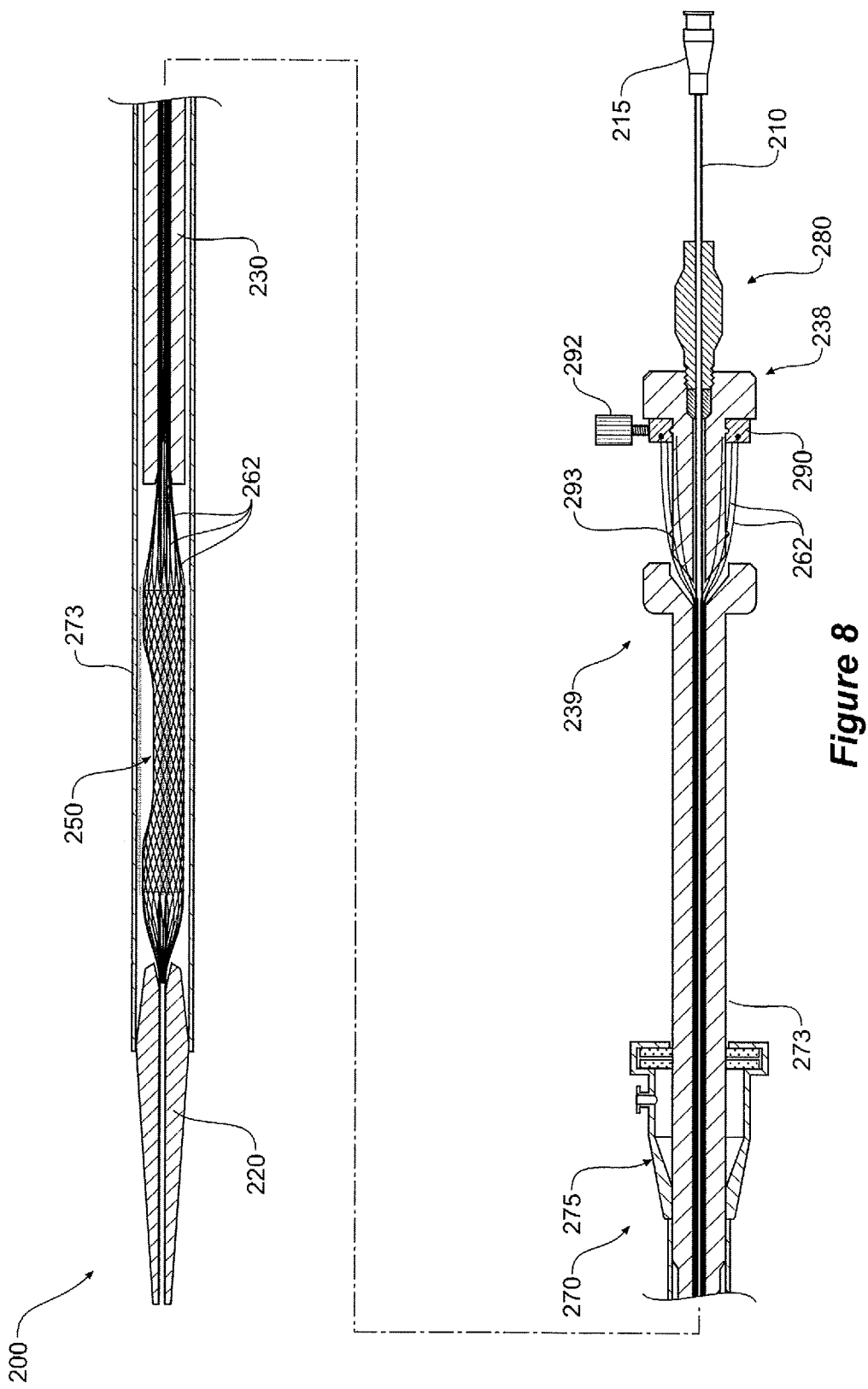
FIG. 8 is a similar view to that of FIGS. 5, 6 and 7, but shows the medical device in a re-sheathed condition.

Now referring to FIG. 8, the device 200 is shown in its retracted position, the sheath assembly 270 having been moved in a proximal direction away from the handle 238 such that the sheath 273 covers the temporary stent assembly 250. The sheath assembly 270 is disposed over the pusher 230 in the same arrangement of the sheath assembly 170 and pusher 130 of the first embodiment described above. The sheath assembly 270 includes a sheath manipulator 275 of the distal end thereof. The sheath assembly includes a haemostatic seal assembly 177 (such as a Captor™ valve) and a flushing port 179, both at a distal end thereof.

A Luer lock connector 215 is also shown in FIGS. 5 to 8. As for the first embodiment of the invention, the Luer lock connector 215 allows flushing with sterile saline solution to eliminate air while the device 200 is outside of the patient.

The line manipulator 290 described above and illustrated in FIGS. 5 to 8 is just one example of a means for pulling the distal lines 262 of the temporary stent assembly 250 in a direction away from the tip 220 so as to stretch the temporary stent assembly 250. Other manipulators utilising rotatable components may also be used. For example a screw mechanism may be used to pull the distal lines 262.

Use of the device 100 will now be described with reference to FIGS. 9 to 15. This description is generally applicable to all of the embodiments of the invention described above, but for ease of reference will be described specifically for use with the first embodiment of the invention.

Figure 9:
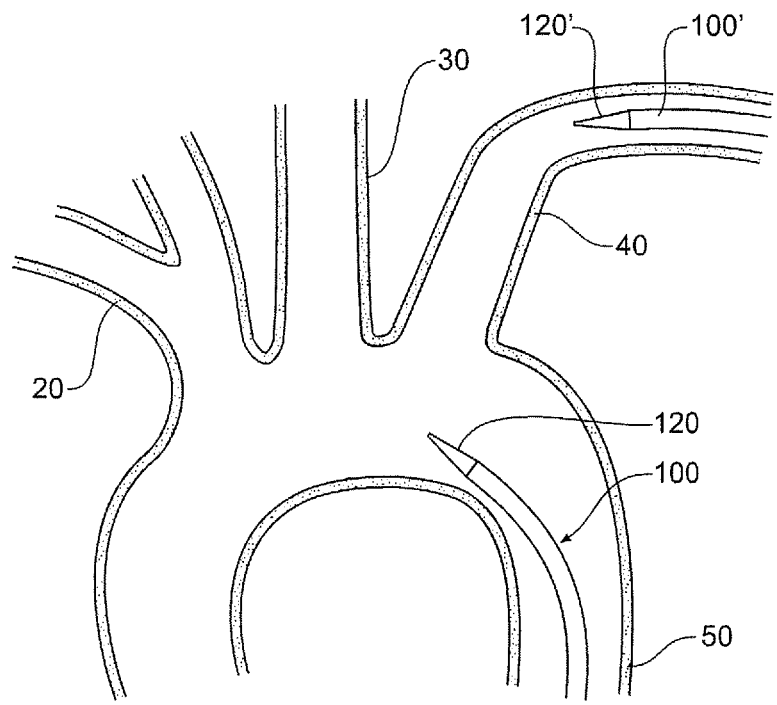
FIG. 9 is a diagrammatic view showing two medical devices according to the invention entering the aortic arch region of a patient.

Referring first to FIG. 9, the aortic arch of a human is illustrated. The brachiocephalic artery 20, common carotid artery 30, subclavian artery 40 and descending aorta 50 are all shown. A portion of a first medical device 100, including its tip 120 is shown within the descending aorta 50. A portion of a second medical device 100', including its tip 120' is shown within the subclavian artery 40. Deployment of the medical devices 100, 100' illustrated can be achieved using well known surgical techniques, including those based on the Seldinger wire technique. This technique involves creating a surgical opening in an artery with a needle or trocar and inserting a wire guide into the artery through a bore of the needle. The needle can be withdrawn, leaving the wire guide in place.

Again referring to FIG. 9, the medical device 100 may be deployed through an incision in the femoral artery of the patient. The medical device is inserted over a guide wire (not shown) into the femoral artery and then is advanced over the guide wire through the position shown in FIG. 9 to the position shown in FIG. 10.

Figure 10:
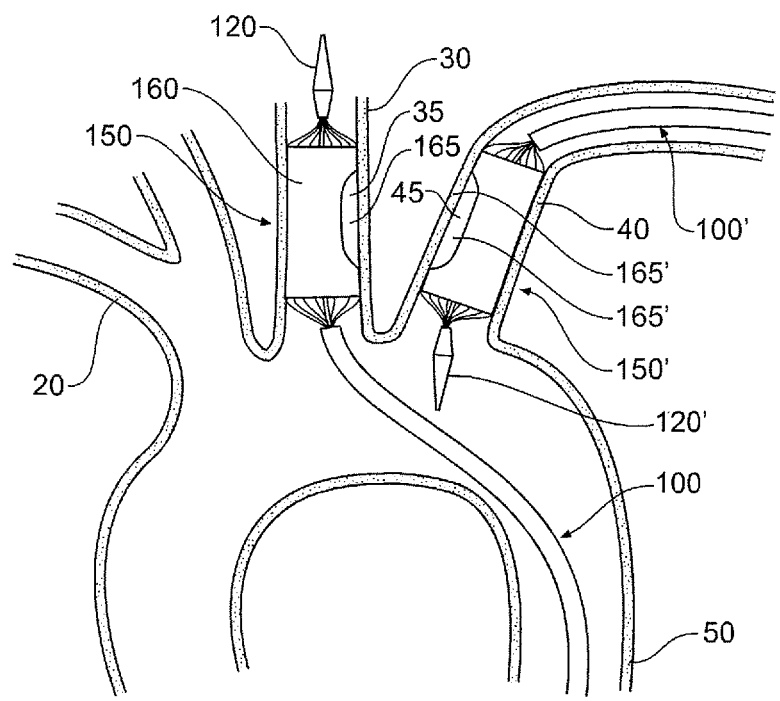
FIG. 10 is a similar view to that of FIG. 9, but shows the medical devices deployed within the common carotid artery and the left subclavian artery.

FIG. 10 is a similar figure to that of 9 but shows further detail of a step of a method of establishing a bypass graft between two arteries 30 and 40. This step is deploying a first temporary stent assembly 150 into a first target artery 30, in this case the common carotid artery 30. This first temporary stent assembly is the stent assembly 150 illustrated in FIGS. 1 to 4. It has a covered portion 160 having a first proximal sealing zone 153, a first distal sealing zone 163 and a first recess 165 between the first proximal and distal sealing zones 153,163.

FIG. 10 also shows a step of deploying a second temporary stent assembly 150' into a second target artery, in this case, the subclavian artery 40. The second temporary stent assembly 150' has a second covered portion 160' having a second proximal sealing zone 153', a second distal sealing zone 163' and a second recess 165' between the second proximal and distal sealing zones 153',163'.

The above two steps result in the creation of pockets 35 and 45. With the arrangement shown in FIGS. 10 and 10A, blood is able to flow through gaps between the lines of the stent assemblies and along the inside of a lumen formed within the covered portion 160 out through the proximal lines 152. At the same time the pocket 35 is sealed off from blood flow. This enables the installation of a anastomosis stent 70 between the first and second target arteries 30,40 as is shown progressively in FIGS. 11 and 12.

Referring again to FIG. 11, incisions 32 and 42 are made to allow fluid communication from artery 30 to artery 40 through anastomosis stent 70.

Figure 13:
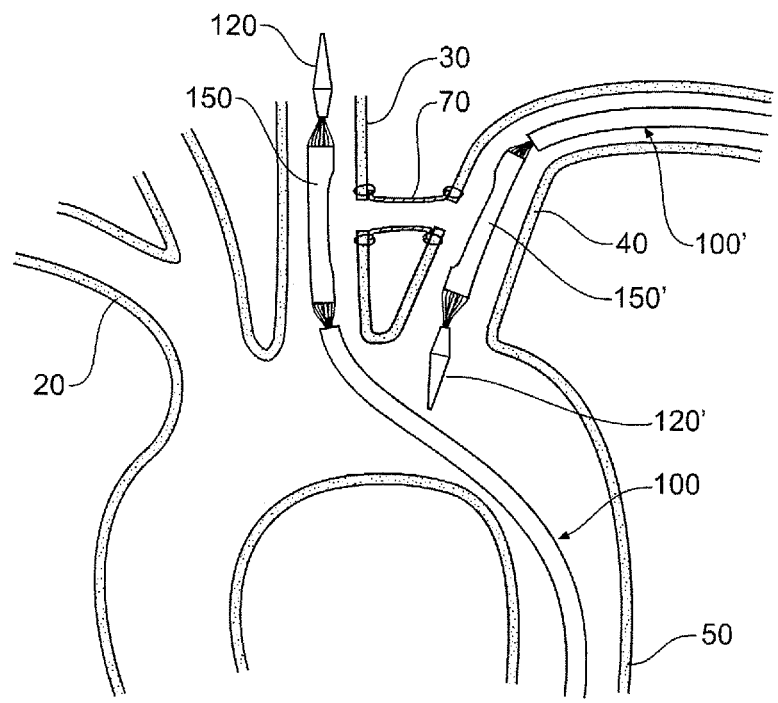
FIG. 13 is a similar view to FIG. 12, but shows the medical devices of the invention being readied for re-sheathing.
Figure 14:
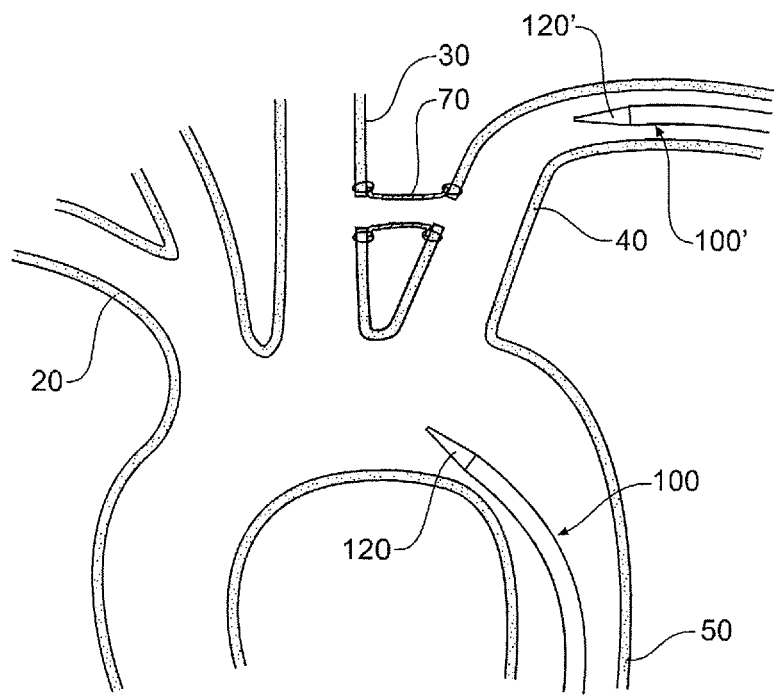
FIG. 14 is a similar view to FIG. 13, but shows the medical devices being retracted.

Once the anastomosis 70 is in place, the first and second temporary stent assemblies 150,150' can be retrieved, as is illustrated in FIGS. 13 and 14. The gradual transition in diameter of the uncovered portion of the temporary stent assembly 150 facilitates re-sheathing with a smooth action aimed at minimizing plaque displacement from the vessel wall.

Figure 15:
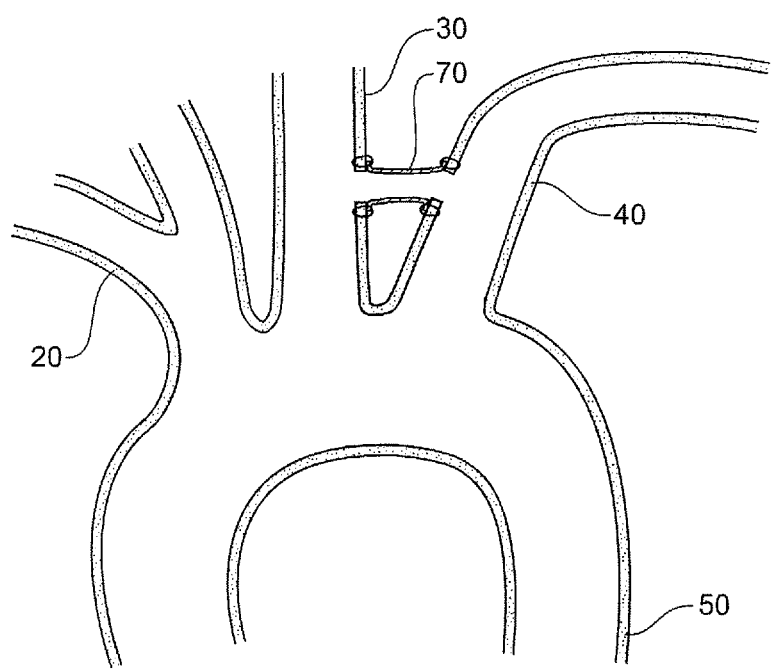
FIG. 15 is a similar view to FIG. 14, but shows the repaired anatomy after the medical devices of the invention have been removed.

The final arrangement within the anatomy is shown in FIG. 15 with the anastomosis stent 70 in place between the common carotid artery 30 and the left subclavian artery 40.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A medical device for temporary deployment into a bodily lumen, the medical device comprising:
    a guide wire cannula having a proximal end and a distal end;
    a tip attached to the proximal end of the guide wire cannula;
    a pusher having a proximal and a distal end, the pusher having a through-bore disposed around the guide wire cannula; and
    a temporary stent assembly having a proximal end attached to the tip and a distal end adjacent to the proximal end of the pusher, the temporary stent assembly comprising a covered portion, the covered portion having a proximal sealing zone, a distal sealing zone and a recess between the proximal and distal sealing zones; and
    a sheath assembly disposed over the pusher, the sheath assembly comprising: a sheath manipulator and a seal assembly at a distal end thereof; and a sheath extending proximally from the sheath manipulator, the seal assembly operable to minimize the egress of blood from the sheath assembly,
    whereby the sheath assembly is slidably movable with respect to the pusher from a first position in which the sheath covers the temporary stent assembly to a second position in which at least the covered portion of the temporary stent assembly is uncovered by the sheath,
    wherein the temporary stent assembly is longitudinally stretchable from a deployable position to a re-sheathable position.

2. The medical device as claimed in claim 1 wherein the temporary stent assembly comprises a plurality of proximal connecting lines extending from the tip to the covered portion and a plurality of distal connecting lines extending from the covered portion to the pusher.

3. The medical device as claimed in claim 2 wherein the temporary stent assembly is self-expanding.

4. The medical device as claimed in claim 3 wherein the covered portion comprises a blood impermeable material supported by woven metal, the woven metal operable to self-expand the blood impermeable material.

5. The medical device as claimed in claim 2 wherein the proximal connecting lines and the distal connecting lines comprise wire lines.

6. The medical device as claimed in claim 5 wherein the wire lines comprise nitinol wire.

7. The medical device as claimed in claim 1 wherein the recess is shaped such that, in use within an artery, a pocket is formed between the proximal and distal sealing zones of the covered portion.

8. The medical device as claimed in claim 1 wherein the proximal sealing zone has a first minimum perimeter and the recess has a second minimum perimeter, the second minimum perimeter shorter than the first minimum perimeter.

9. The medical device as claimed in claim 1 wherein the tip is extendible from the pusher so as to stretch the temporary stent assembly.

10. The medical device as claimed in claim 9 wherein the pusher comprises a gripable handle at its distal end.

11. The medical device as claimed in claim 10 wherein the pusher includes a mechanism for selectively holding the guide wire cannula to the handle and releasing the guide wire cannula from the handle.

12. The medical device as claimed in claim 1 comprising a line manipulator located at the distal end of the pusher, the line manipulator manipulable to pull the distal lines of the temporary stent assembly in a direction away from the tip as to stretch the temporary stent assembly.

13. The medical device as claimed in claim 12 wherein the distal lines of the temporary stent assembly pass through the through-bore.

14. The medical device as claimed in claim 12 wherein the line manipulator is lockable in a deploying position in which the temporary stent assembly is not stretched.

15. The medical device as claimed in claim 12 wherein the line manipulator is lockable in a re-sheathable position in which the temporary stent assembly is stretched.

* * * * *